United States Patent [19]

Baker et al.

[11] Patent Number: 4,838,862
[45] Date of Patent: Jun. 13, 1989

[54] PORTABLE CONTROLLED RELEASE OSMOTIC INFUSION DEVICE

[75] Inventors: Richard Baker, Menlo Park; Verne Helm, Santa Clara; Paul Shrock, Mt. View, all of Calif.

[73] Assignee: Pharmetrix Corp., Menlo Park, Calif.

[21] Appl. No.: 892,991

[22] Filed: Aug. 4, 1986

[51] Int. Cl.⁴ .............................................. A61K 9/22
[52] U.S. Cl. .................................. 604/892.1; 604/87; 604/244
[58] Field of Search ............... 604/891, 892, 131, 140, 604/141, 143, 148, 82, 86, 87, 89, 236, 237, 244, 93, 185

[56] References Cited

U.S. PATENT DOCUMENTS

| | | | |
|---|---|---|---|
| 3,604,417 | 9/1971 | Stolzenberg | 604/143 |
| 4,140,122 | 2/1979 | Kühl et al. | 604/891 |
| 4,193,398 | 3/1980 | Refson | 604/131 |
| 4,217,894 | 8/1980 | Franetzk | 604/131 |
| 4,320,754 | 3/1982 | Theeuwes | 604/892 |
| 4,410,328 | 10/1983 | Theeuwess | 604/892 |
| 4,474,048 | 10/1984 | Eckenhoff et al. | 604/131 |
| 4,474,575 | 10/1984 | Eckenhoff et al. | 604/131 |
| 4,529,403 | 7/1985 | Kamstra | 604/136 |
| 4,552,561 | 11/1985 | Eckenhoff et al. | 604/131 |
| 4,608,048 | 8/1986 | Cortese et al. | 604/892 |

Primary Examiner—C. Fred Rosenbaum
Assistant Examiner—Mark F. Colosimo
Attorney, Agent, or Firm—J. Farrant

[57] ABSTRACT

A portable controlled release osmotic infusion device, which can be activated on demand by the user, comprising a rigid housing containing:

a. a fluid-imbibing assembly, comprising a solvent-containing chamber and a solute-containing chamber; the two chambers separated by a rigid semipermeable membrane covered by a thin taut foil seal, b. a drug-containing chamber separated from the fluid-imbibing assembly by a leakproof impermeable elastic diaphragm, which expands into the drug-containing chamber in use and drives the drug through a dispersing orifice at a steady rate, and c. an activating device which ruptures the foil seal described in (a) above and initiates the osmotic action of the device.

The osmotic device is filled with drug in solution or suspended form during manufacture and can be stored without deterioration of the contents for prolonged periods of time.

11 Claims, 9 Drawing Sheets

PORTABLE CONTROLLED RELEASE OSMOTIC INFUSION DEVICE

This invention was made with Government support under Contract Number N0014-84-C-0362, awarded by the U.S. Navy, Office of Naval Research. The Government has certain rights in this invention.

BACKGROUND OF THE INVENTION

1. Field of the Invention

This invention relates to a portable infusion device which is carried externally or internally by the user and which constitutes a controlled release system capable of delivering a steady dose of drug or other pharmaceutical agent for a prolonged period.

2. Description of the Prior Art

Many kinds of parenteral drug therapy require continuous delivery in preference to single or multiple injections. Benefits that accrue from continuous therapy may include, for instance, reduction of toxic or other side effects associated with sharp pulses of drug, significant improvement in the effectiveness of the therapy, and increased comfort of the patient. The traditional manner of administering sustained parenteral treatments is an intravenous drip. While this may be perfectly acceptable in a hospital environment, it obviously imposes severe restrictions on the activity of the recipient. As a result, considerable research over the last few years has been devoted to the development of small portable infusion pumps. The simplest of these have clockwork or battery operated motors, which drive syringe or peristaltic pumps, and are strapped to the user with a harness. A typical example is described by A. J. Handley, in "Portable Heparin Injector", *The Lancet*, 2, p. 313 (1970). A more recent development in the art is the implantable miniature pump. Such pumps have been explored particularly for the treatment of diabetes by continuous insulin therapy, and in addition to peristaltic or syringe devices, others powered for instance by the elastic tension of an inflated rubber balloon or the vapor pressure of a liquified propellant have also been used. For a review of these pumps, see M. V. Sefton, "Implantable Pumps", *Medical Applications of Controlled Release Vol* 1, R. S. Langer and D. L. Wise (eds), CRC Press, Boca Raton FL (1984).

The disadvantages of these pumps are that they are quite complex and costly to manufacture, making them inappropriate for widespread application. Most of them are also designed to deliver relatively large quantities of fluid and do not dispense small volumes of the order of a few milliliters effectively.

At the other end of the scale a range of tiny osmotic pumps based on the principle of the Rose-Nelson pump described in detail below has been devised. These are activated by imbibition of water from the surrounding environment and are designed for implantation or ingestion into the body, such that the absorption of body fluids is the triggering mechanism. A typical example is disclosed by F. Theeuwes in U. S. Pat. No. 3,760,984 (September 1973). These pumps are available commercially from Alza Corporation of Palo Alto, Calif., under the name Alzet ®. Theeuwes has also developed a further simplification of the Rose-Nelson concept which can be prepared by a simple tabletting machine. (U.S. Pat. No. 3,845,770 (November 1974)). These miniosmotic pumps and tablets are capable of delivering quantities of drug around a milliliter or so at dosage rates of the order of 1 $\mu$l per hour. They are simple and cheap to produce, but are generally limited to internal use because of their need to reside in an aqueous environment.

The advantages of simplicity, reliability and small size offered by Rose-Nelson type devices have been employed in the art only to a limited extent in osmotic pumps intended for external use. U.S. Pat. No. 3,604,417 (September 1971) discloses a modification of the Rose-Nelson pump in which a movable piston replaces the elastic diaphragm separating the drug and salt chamber, and both the drug and salt are loaded into the pump as solutions. U.S. Pat. No. 4,474,048 discloses another modification employing an impermeable elastic wall, and a movable end wall which can be screwed in to deliver a pulse dose of the contained drug at any time during the operation of the pump. U.S. Pat. No. 4,474,575 is a variant of U.S. Pat. No. 4,474,048 where the flow rate of the dispensed agent can be varied by altering the area of the semipermeable membrane exposed to the water chamber.

U.S. Pat. No. 4,552,561 discloses a pump assembly for use with a small osmotic pump, which can be filled in advance of use with the active agent to be dispensed. The action of the pump is initiated by filling the lower chamber of the housing with a hydrogel. Once the pump is in action, an optional mechanism for delivering pulse doses can be employed.

All of the above mentioned patents disclose pumps which are self driven and begin to operate as soon as they are primed with the contents of the several chambers. However in many instances it would be desirable to load the pump and store it until needed. This would enable the pump to be dispensed by a pharmacist for example, instead of requiring installation in a hospital setting. Furthermore the ability to store the filled pump, distribute to potential users, and activate very rapidly on demand would extend the field of use considerably to include such important medical emergencies as attack by toxic agents in warfare, severe allergic reactions and so on.

SUMMARY OF THE INVENTION

It is a principal object of the present invention then to provide a portable controlled release osmotic infusion pump which can be activated quickly and simply on demand.

A further object is to provide such a pump that can be stored, complete with drug and pump activating fluid, for prolonged periods without deterioration.

Yet another object is that the said pump be inexpensive and straightforward to manufacture.

Additional objects and advantages of the present invention will be set forth in part in the description which follows and in part will be obvious from the description or can be learned by practice of the invention. The objects and advantages are achieved by means of the devices, mechanisms and combinations particularly pointed out in the appended claims.

To achieve the foregoing objects, the present invention provides a portable controlled release infusion pump based on the principle of the osmotic pump originally conceived by Rose and Nelson in the 1950s. (S. Rose and J. F. Nelson, "A Continuous Long-Term Injector", *Austral. J. exp Biol.* 33, pp 415–420 (1955)). A Rose-Nelson pump consists of three chambers: a salt chamber containing excess solid salt, a drug chamber and a water chamber. The salt and water compartments are separated by a rigid membrane permeable to water but impermeable to salt; the salt and drug chambers are separated by a rubber diaphragm. In operation water is imbibed osmotically into the salt chamber causing the rubber diaphragm to expand into the drug chamber and forcing the drug out through a delivery orifice. Depending on the salt used, the osmotic pressure developed by this type of pump is usually between 50 and 200 atmospheres. The pressure required to pump the drug from the device is small in comparison, and hence the drug delivery rate remains constant as long as some excess undissolved salt remains in the salt chamber.

The portable infusion pump disclosed herein comprises a rigid outer housing containing a fluid-imbibing assembly and a drug chamber, and incorporating an activator mechanism. The outer housing can be metal or plastic, for example, and would normally be made by any conventional mass-production technique. The fluid imbibing assembly consists of a solvent-containing compartment and a solute-containing compartment, separated by a rigid semipermeable membrane. The membrane is isolated from the solvent chamber by a thin foil seal held rigid and taut by a stainless steel washer. When the foil is ruptured the porous wick draws the osmotic fluid into contact with the membrane and the osmotic pumping action begins. The preferred osmotic fluid in the context of the present invention is water, and as such both the general and detailed descriptions of the invention herein refer to the osmotic fluid as water and the chamber within which the fluid is initially contained as the water chamber. It should be borne in mind, however, that other fluids may be preferable in some circumstances, and the scope of the invention is intended to encompass any combination of solute, solvent and semipermeable membrane that can generate an osmotic pressure driving force for the pump. The activator mechanism may be a simple plunger and needle, which works by puncturing the foil seal; however many different activating devices are envisaged and will be discussed in detail below, it is intended that the scope of the present invention should encompass any actuator. The combination of solute, solvent and membrane is tailored to the desired flow characteristics. The drug-containing chamber is separated from the fluid imbibing assembly by an elastic diaphragm, which differs from the diaphragms currently extant in the art in that it is more truly impermeable. Standard elastomers such as latex rubber, butyl rubber or the styrene-butadiene copolymers are not sufficiently impermeable to prevent long-term migration of the contents of the drug chamber through to the salt chamber. Such migration is obviously unacceptable if the pump is to be employed as a simple, off-the-shelf, user-activated device.

The foregoing general description and the following detailed description are exemplary and explanatory, but are not restrictive of the invention.

BRIEF DESCRIPTION OF THE DRAWINGS

FIG. 4C shows the position of the needle when the pump is in use.

FIG. 5C shows the activating valve in the open position.

DETAILED DESCRIPTION OF THE INVENTION

"Drug" as used herein broadly includes physiologically or pharmacologically active substances for producing a localized effect at the administration site or a systemic effect at a site remote from the administration site.

Figure 1:
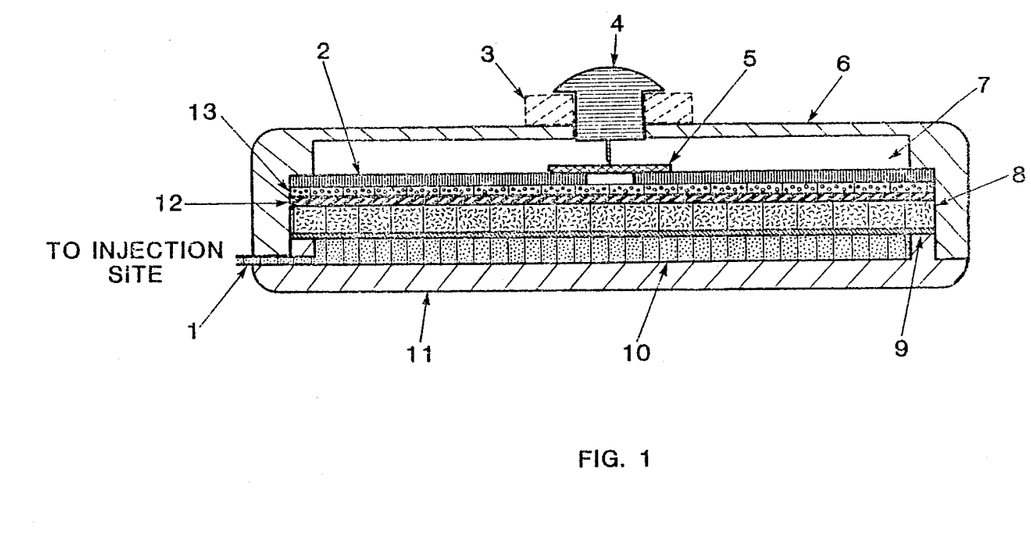
FIG. 1 is a sectional view of a basic embodiment of the invention.

The objects described above are achieved by a device based on the osmotic pumping system first proposed by Rose and Nelson in 1955. Referring now to the drawings, a basic embodiment of the invention is shown in FIG. 1. The outer housing, 6, is rigid and should be made of a substance that is non irritating to the skin and non-reactive and impervious to the salts, solutions and agents contained. Embodiments intended for implantation should be biocompatible. Preferably the chosen material should be amenable to reliable, inexpensive mass-production. Typical materials that could be used include for example stainless steel, aluminum, polyolefins, polycarbonate and the like. It may be desirable to machine a small hole in the top surface of the housing, which is then plugged with a hydrophobic, air-permeable material such as porous teflon, so that a vacuum does not build up in the water chamber, 7, as the water is exhausted. Similar criteria to those above apply to the choice of material for the bottom plate, 11. Optionally this plate may be adhesive on its outer surface to assist in holding the pump in place on the body. The actuator shown in FIG. 1 is a plunger and needle. The pumping action is started by removing the protective spacer, 3, and depressing the raised button portion of the plunger on the top of the device. The pressure thus applied causes the plunger, 4, to puncture the foil seal, 5. Optionally an injection needle may be connected to the activating plunger, such that depressing the plunger pushes the injection needle through the skin. This type of activator also delivers a small priming dose of the active agent or drug to the user when the button is depressed. Alternatively the pump may be used in conjunction with a standard commercial subcutaneous drug delivery set, for example, the Sub-Q-Set ®, obtainable from Travenol Laboratories, Deerfield, IL. With the foil seal broken, the porous wick, 13, draws water by capillary action from the water chamber, 7, into contact with the semipermeable membrane, 12. Water is then imbibed osmotically into the salt chamber, 8. The elastic diaphragm, 9, expands into the drug chamber, 10, forcing the drug out through the delivery port, 1, to the injection or administration site.

Figure 2:
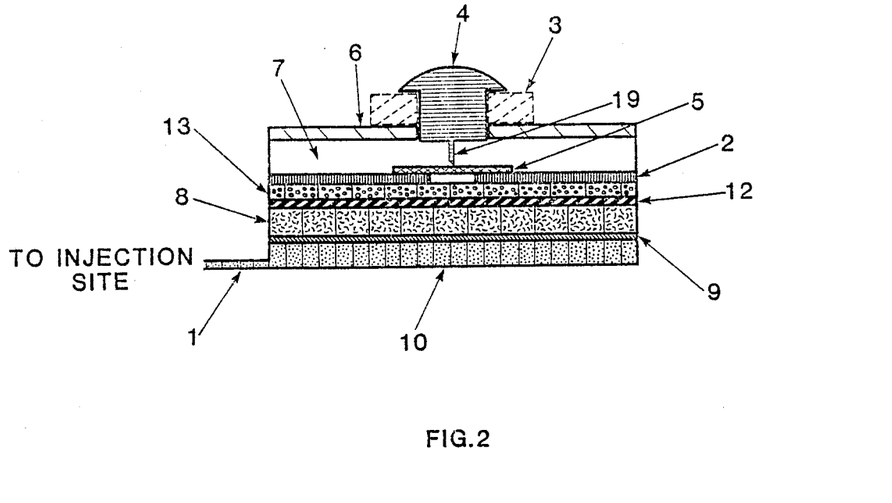
FIG. 2 is a schematic representation of an embodiment of the invention activated by a puncture mechanism.
Figure 3:
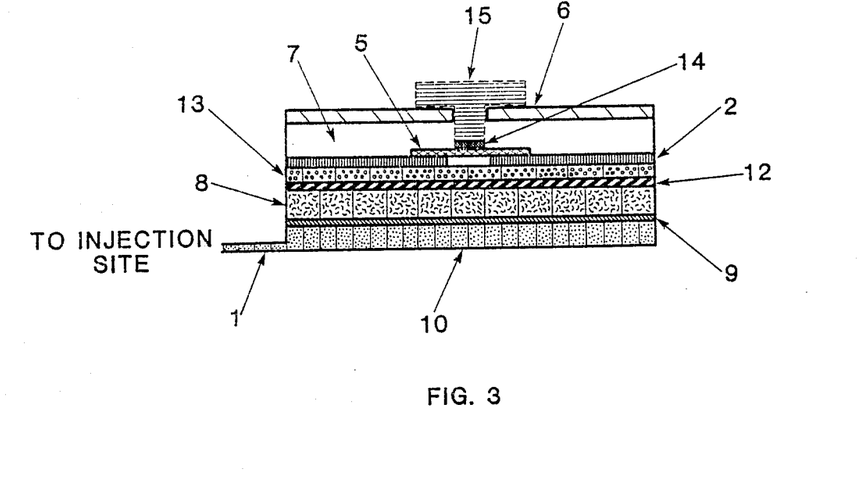
FIG. 3 is a schematic representation of an embodiment of the invention activated by a ripping mechanism.
Figure 4A:
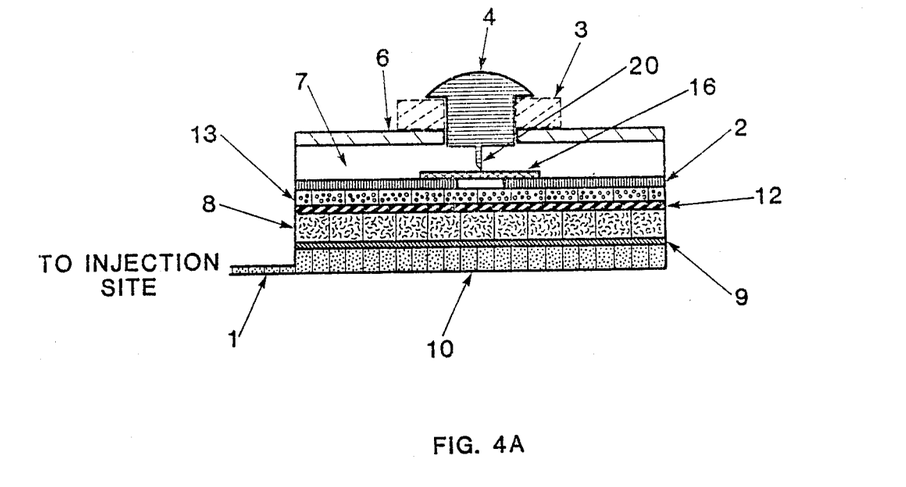
FIG. 4A is a schematic representation of an embodiment of the invention activated by a septum-piercing hollow needle.
Figure 4B:
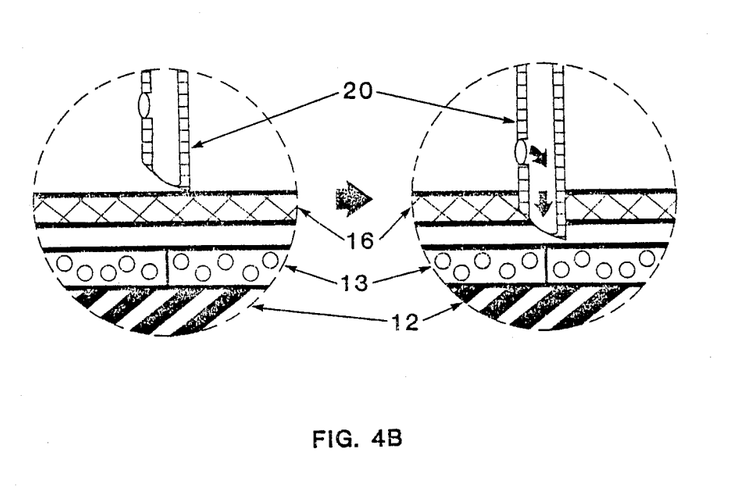
FIG. 4B shows an expanded view of the septum-piercing needle of FIG. 4A.
Figure 5A:
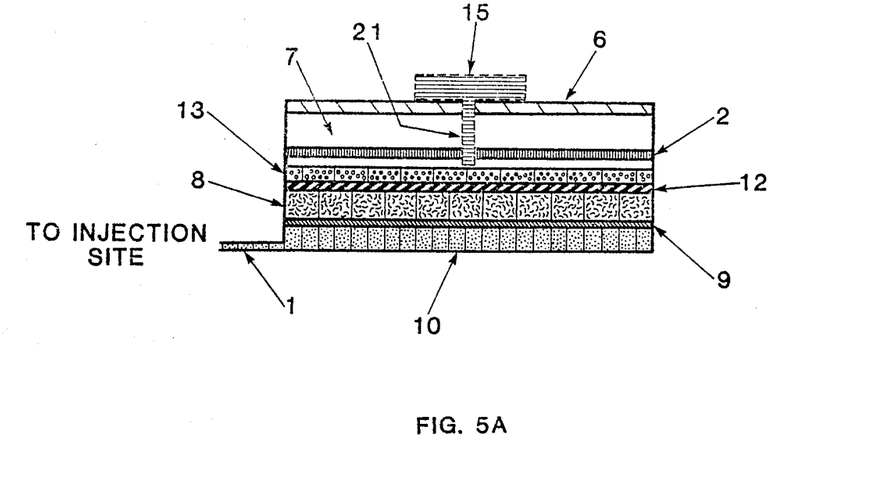
FIG. 5A is a schematic representation of an embodiment of the invention activated by a valve.
Figure 5B:
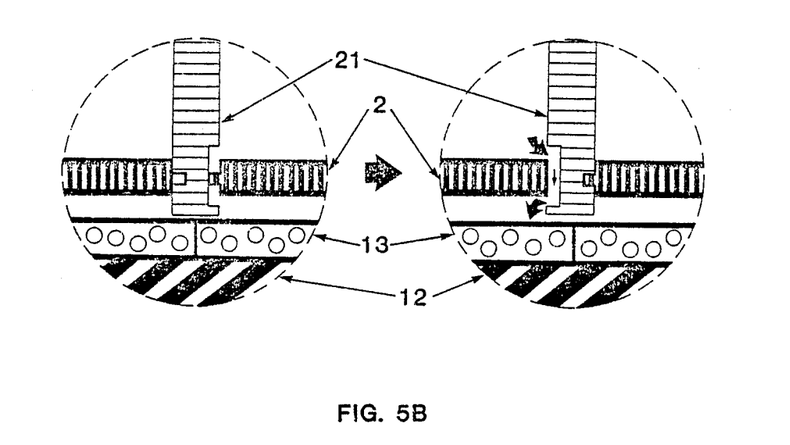
FIG. 5B shows an expanded view of the activating valve of FIG. 5A.

FIGS. 2, 3, 4 and 5 are schematic representations of some possible alternative activating mechanisms. FIG. 2 shows the piercing mechanism as described in the embodiment above. The plunger has a needle-like protrusion, 19, extending into the water chamber. The foil seal, 5, is held taut by the rigid support plate, 2. This plate also serves to strengthen the semipermeable membrane, 12, and prevent it being pushed into the water chamber by the osmotic pressure of the salt solution during operation of the pump. Depressing the plunger causes the needle, 19, to pierce the foil seal, allowing water to come into contact with the porous wick, 13. The pump then operates as described above. FIG. 3 shows a scheme in which the seal, normally aluminum foil, separating the water chamber from the wick is connected to a rotatable dial, 15, at the top of the pump by means of epoxy adhesive, 14. When the dial is turned, the foil is torn and the pumping action commences as described above. This mechanism may be preferable in some instances since a larger opening from the water chamber to the wick is produced, so response time may be less than that obtained with the puncture device. The possibility of the needle damaging the membrane is also eliminated. FIG. 4A shows a mechanism incorporating a rubber septum, 16, and a hollow needle, 20. Depressing the plunger causes the needle to pierce the septum and allows water to flow into contact with the wick, as shown in FIGS. 4B and 4C, initiating the pumping as before. FIG. 5A illustrates yet another possibility using a valve, 21. During storage the valve is in the closed position, as shown in FIG. 5B. To activate the pump, the dial is turned through 180 degrees, so that the valve is now in the fully open position, as shown in FIG. 5C. Water may then contact the porous wick as before. It should be apparent that many different mechanical solutions to the problem of activation are possible and that the methods described are not exclusive of any others. The novelty of the invention includes the concept of an activating device and the scope of the invention is intended to encompass any actuator.

Figure 6:
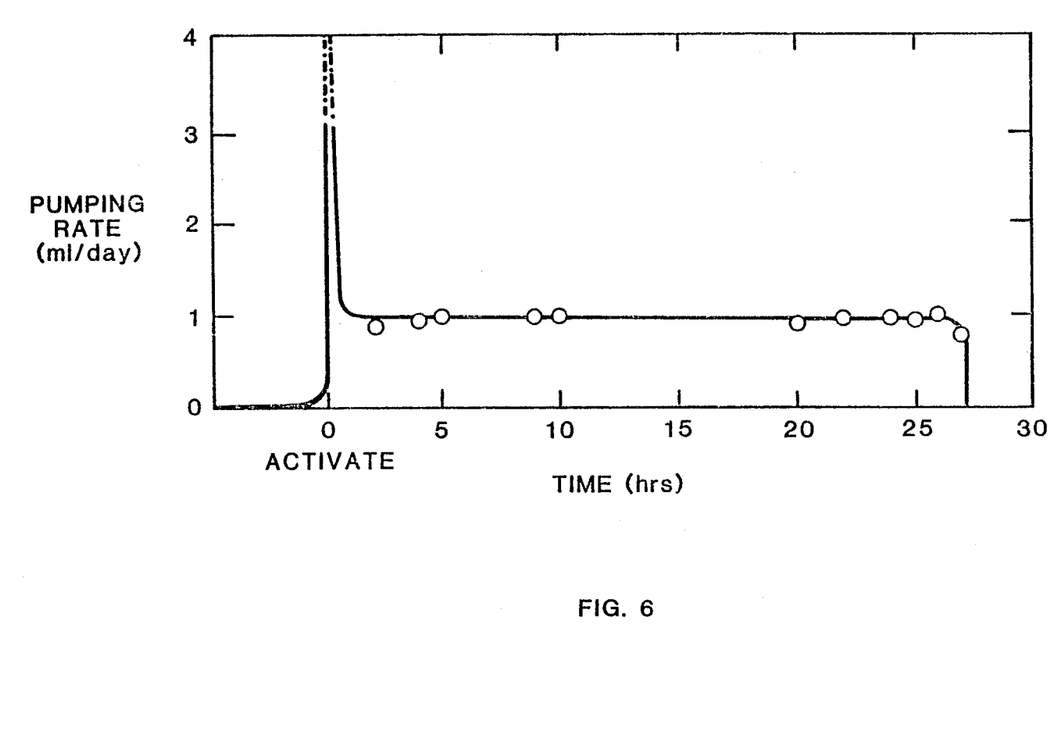
FIG. 6 is a graphic representation of the pumping profile of the embodiment of FIG. 1.

A typical pumping profile for the basic embodiment of FIG. 1 is shown graphically in FIG. 6. The pumping rate depends on the membrane and salt chosen. The steady state pumping rate is given by $$dv/dt = Ak\pi/l$$

where dV/dt is the volume flow of drug from the pump and is equal to the volume flow of water into the salt chamber, A is the membrane area, k is the osmotic permeability of water through the membrane in cm$^3$·cm/cm$^2$·atm·hr, l is the membrane thickness and $\pi$ is the osmotic pressure of the saturated salt solution in the salt chamber. From this equation it can be seen that the delivery rate of pump depends on the membrane area, thickness and permeability. Hence the choice of a suitable membrane material is essential to good performance of the pump. A preferred choice is a membrane made from one of the cellulose esters or ethers, such as cellulose acetate or cellulose butyrate. Cellulose acetate has a long record of use in membrane applications and can easily be formed into thin films of reproducable thickness with standard solution casting techniques, making it a particularly preferred choice.

The osmotic pressure of the saturated salt solution should be large compared to the pressure required to pump the drug from the device, and the amount of salt used should be such that excess solid salt remains for the life of the pump. In this way a constant drug delivery rate can be sustained throughout the period of use. Furthermore, as can be seen from FIG. 6, the pump stops abruptly when the contents of the water chamber are exhausted. This gives the pump of the present invention a particular advantage, in that so long as the volume of the water chamber is less than that of the drug chamber, there is no risk of the high osmotic pressures involved causing the diaphragm to rupture, thereby pumping salt solution into the user. The osmotic pressure of the standard salt solution depends on the molecular weight and solubility of the salt; for most common salts it is in the range 50 to 200 atmospheres. A wide range of appropriate solutes is disclosed in U.S. Pat. No. 4,034,756, which is incorporated herein by reference. Preferred salts are sodium chloride, potassium chloride, magnesium sulfate and sodium sulfate. These give a good range of osmotic pressure differences across the membrane and provide a means whereby the flow rate of the pump can be varied to suit the desired application. Another advantage of the osmotic pump is that the high pressure under which the pump operates is large enough to overcome any back pressure that may build up as a result of a blockage in the delivery needle. These types of blockages are a not infrequent source of problems in other types of miniature infusion pumps.

Since the essence of the present invention is that the infusion device can be filled, stored for extended periods of time and then activated on demand, it is essential that the expandable elastic diaphragm be completely impermeable to the chosen drug, otherwise slow migration of the fluids from the drug chamber into the salt chamber will cause the device to deteriorate during storage. A wide range of standard impermeable materials with good elastomeric properties is known in the art, such as latex rubber, polyisoprene, butyl rubber, nitrile rubber, copolymers of styrene/butadiene and the like. When storage periods of months or years are envisaged however, these materials may be less desirable. A preferred alternative is to use a standard elastomer faced with a thin layer of aluminum foil, which will rupture as soon as the elastic diaphragm begins to expand. A second preferred alternative is to use a metallized elastic material, formed by vacuum deposition of aluminum or other metals on an elastic rubber based material.

The contents of the drug chamber may be any agent or combination of agents that would normally be administered by the parenteral route. A preferred embodiment employs a drug dissolved or suspended in an appropriate solvent, generally water. Another preferred embodiment, which is particularly desirable if the drug to be used has limited stability in solution, employs lyophilized drug. In this case water would be added to the drug chamber by the pharmacist, by injection through a small septum in the wall of the drug chamber, immediately prior to dispensing. Drugs that could be used in this way include, but are not limited to, protein and polypeptide drugs such as insulin, growth hormones, interferon, interleukin2, luteinizing hormone-releasing hormone (LHRH) and so on.

Figure 9A:
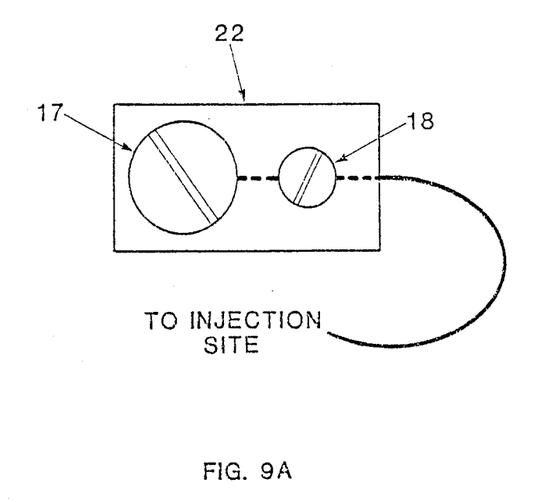
FIG. 9A shows the top view of an embodiment of the invention incorporating a device for delivering an initial priming dose of the drug.
Figure 9B:
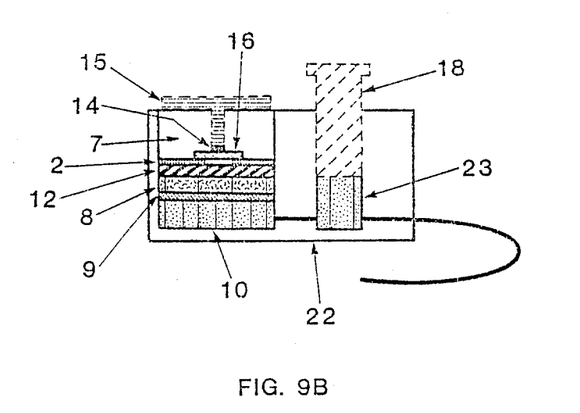
FIG. 9B shows a sectional view of the embodiment of FIG. 9A.

Optionally any of the embodiments described above can incorporate the capability to deliver an initial priming dose for rapid initial therapy, followed by the prolonged period of slow controlled release. Various methods of accomplishing this end may be envisaged; a typical method is shown in FIG. 9, which serves to illustrate the principle. Referring now to FIG. 9, the basic embodiment of FIG. 1 is extended to incorporate a priming dose mechanism, 18, which is built into an outer casing, 22, alongside the osmotic pump, 17, as shown in top view in FIG. 9A. As can be seen from FIG. 9B, the priming dose mechanism is in contact with a secondary drug chamber, 23. Operating the mechanism reduces the volume of the secondary drug chamber, and the corresponding volume of drug is delivered to the user. The priming dose mechanism may be operated by the screw principle, such that rotating the part protruding from the outer casing threads the mechanism further down into the casing and reduces the volume of the secondary drug chamber. Alternatively it could be in the form of a spring-loaded plunger, a sliding valve, a piston and so on. This initial dose is followed by the slow controlled release delivery as the osmotic action of the pump begins.

The present invention would extend the field of use of portable infusion devices considerably. In particular, areas of medicine to which the existing art cannot be applied, could be addressed. These areas include, for instance, emergencies such as severe allergic reactions. Patients with a known history of allergy problems could keep the primed device on hand for use as necessary. Another desirable application is the administration of toxic antidotes. A DTIC report, "U.S. Army Chemical Effects Data Requirements", MONA-WE-1-82(1982) states that current antidotes to chemical warfare agents are unacceptable. Several of the new antidotes under development must be delivered at a slow controlled rate over a period of one to three days. The present invention represents a novel solution to the problem of controlled release therapy under field conditions. The device could be filled months or years in advance and issued to service personnel prior to battle. Existing portable infusion pumps could not be used in this context. Long-term pain control therapy, treatment of infectious diseases, and other areas of medicine where portable infusion devices are currently employed, could also be addressed with this pump.

The following examples are given by way of illustration to further explain the principles of the invention. These examples are merely illustrative and are not to be understood as limiting the scope and underlying principles of the invention in any way.

EXAMPLE 1

The basic embodiment of the invention shown in FIG. 1 was prepared. The body of the pump was machined from aluminum. The pump was 1.3 cm thick, 3.5 cm in diameter, and weighed 6.9 grams empty. The semipermeable membrane was cellulose acetate 50 microns thick, formed by casting a solution of cellulose acetate 398.10 (Eastman Kodak Co., Kingsport, Tenn.) dissolved in acetone onto a clean glass plate. The osmotic salt chosen was sodium chloride, the driving fluid water, and the elastic diaphragm was latex rubber faced with a thin disk of aluminum foil. The pumping profile obtained is shown graphically in FIG. 6. There was an initial high release of drug immediately after activation, after which the pump reached its steady state pumping rate of 1.0 ml per day for 27 hours. The pump stopped completely as soon as the water chamber was exhausted, although some drug solution remained in the drug chamber at that point.

EXAMPLE 2

Figure 7:
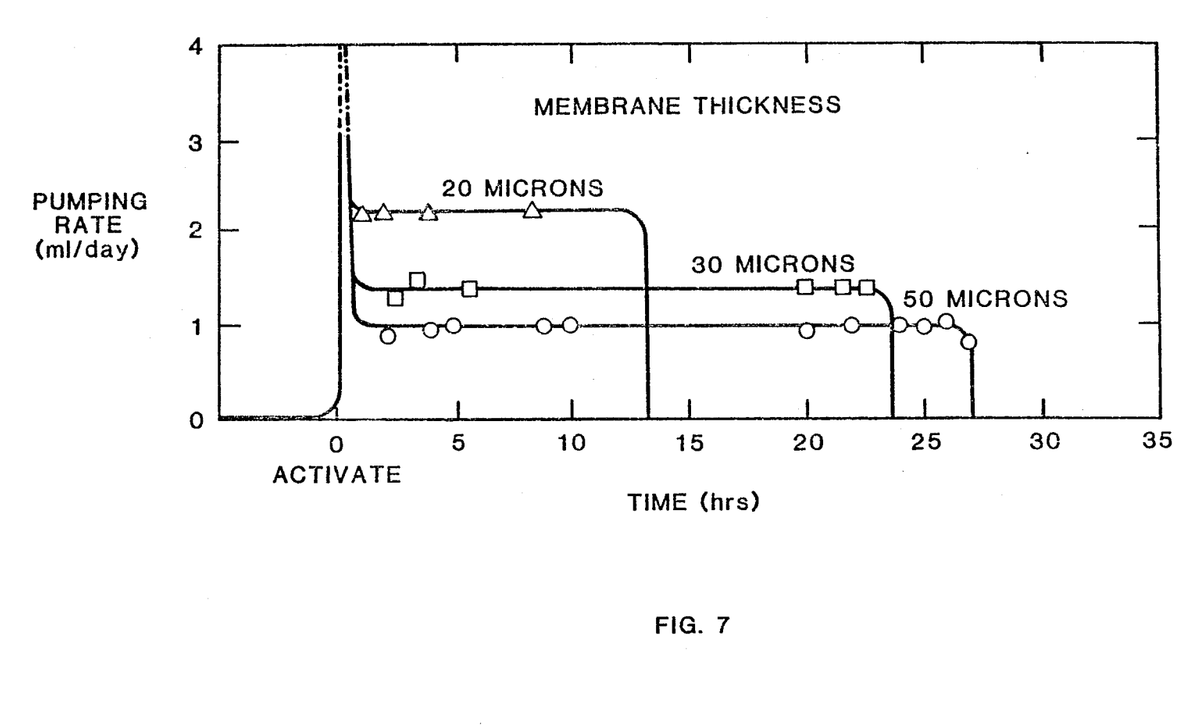
FIG. 7 is a graphic representation of the pumping profile of the embodiment of FIG. 1, using semipermeable membranes of different thickness.
Figure 8:
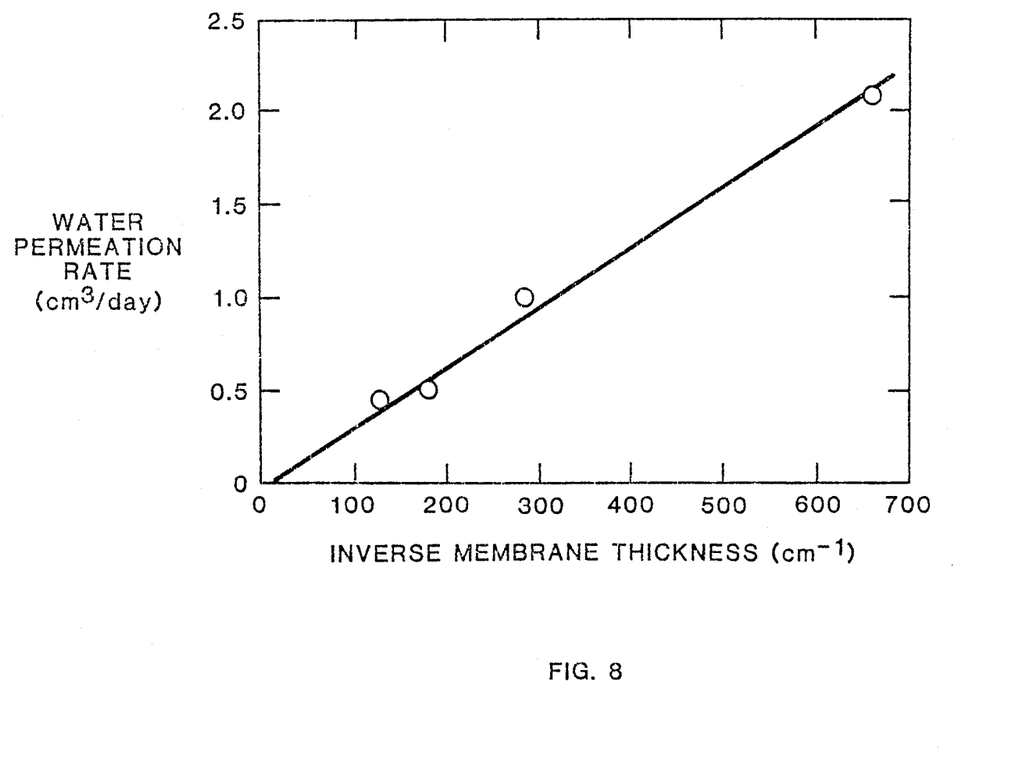
FIG. 8 is a graphic representation of the relationship between pumping rate and membrane thickness.

Embodiments were prepared as described in Example 1. Semipermeable membranes of varying thicknesses, all composed of cellulose acetate, were used. The results obtained are shown graphically in FIG. 7. The pumping rate was found to depend on membrane thickness as shown in FIG. 8. Hence changing the membrane thickness is a method by which the pump can be tailored to deliver a specific drug dosage rate.

EXAMPLE 3

Embodiments were prepared as described in Example 1, using a cellulose acetate membrane 15 microns thick. Four different osmotic salts were used; the driving fluid in each case was water. The results are summarized in Table 1.

TABLE 1

| Salt | Sodium chloride | Potassium chloride | Magnesium sulfate | Sodium sulfate |
|---|---|---|---|---|
| Pumping rate(ml/day) | 2.1 | 1.7 | 1.5 | 0.6 |

From this it can be seen that an appropriate salt may be chosen to fine tune the delivery rate of the pump.

EXAMPLE 4

An embodiment was prepared as described in Example 1, except that in this case the activating mechanism was a dial as shown in FIG. 3. When the dial was turned, the foil was torn and the pump activated. A larger opening form the water chamber to the wick was produced than with the puncture activator. As a result the time delay before pumping began was considerably reduced.

EXAMPLE 5

Embodiments were prepared as described in Example 1. The drug chamber was filled with aqueous glycerin solutions of differing viscosities. The results are shown in Table 2.

TABLE 2

| Drug solution viscosity(centipoise) | 0.9 | 70.0 | 950.0 |
|---|---|---|---|
| Pumping rate (cm$^3$/min) | 0.0040 | 0.0034 | 0.0035 |

Although the viscosity of the glycerin solutions varied by more than a hundredfold, the pumping rate altered by less than 15%. As predicted by theory, the pumping rate was essentially independent of the viscosity of the drug solution.

It will be understood that the above description of the present invention is susceptible to various modifications, changes and adaptations, and the same are intended to be comprehended within the meaning of the range of equivalents of the appended claims.

We claim:

1. A portable controlled release osmotic infusion device comprising:
   (a) a housing, containing;
   (b) a fluid-imbibing unit, comprising a solvent-containing chamber and a solute-containing chamber; the two chambers separated by a semipermeable membrane assembly, said assembly comprising a two-layer laminate of a semipermeable membrane layer and a solute-impermeable sealing layer;

(c) a drug-containing chamber separated from the fluid-imbibing unit by a leakproof impermeable elastic diaphragm; and (d) an activating mechanism which breaks said sealing layer; said activating mechanism being disposed adjacent to, and in contact with, said fluid-imbibing unit;

said portable controlled release osmotic infusion device being characterized in that it may be filled with the contents of said solvent-containing, solute-containing and drug-containing chambers, and stored in an inactive state until required.

2. The device of claim 1, wherein said solute-impermeable sealing layer comprises metal foil and the activating mechanism comprises a puncture device that pierces said solute-impermeable sealing layer.

3. The device of claim 1, wherein said solute-impermeable sealing layer comprises metal foil and the activating mechanism rips said solute-impermeable sealing layer.

4. The device of claim 1, wherein said solute-impermeable sealing layer comprises a septum and the activating mechansim is a hollow needle that pierces said septum.

5. The device of claim 1, wherein said solute-impermeable sealing layer comprises a valve and the activating mechanism opens the valve.

6. The device of claim 1, wherein the elastic diaphragm comprises rubber covered by a layer of metal foil.

7. The device of claim 1, wherein the elastic diaphragm is coated with a vacuum deposited metal film.

8. The device of claim 1, wherein the drug is an antidote to a toxic agent.

9. The device of claim 1, wherein the drug is in the form of a lyophilized solid during storage, and is reconstituted prior to activation.

10. The device of claim 1, wherein the drug is a polypeptide.

11. The device of claim 1, further comprising:
(a) a second drug-containing chamber, separate from, but connected to, the first drug-containing chamber, and
(b) a means for reducing the volume of said second drug-containing chamber.

* * * * *